United States Patent [19]

Igarashi et al.

[11] Patent Number: 5,285,385
[45] Date of Patent: Feb. 8, 1994

[54] SYSTEM FOR DISPLAYING AN ESTIMATED CURRENT SOURCE

[75] Inventors: Yutaka Igarashi, Yokohama; Takaki Shimura, Machida; Takehiko Hayashi, Kawasaki, all of Japan

[73] Assignee: Fujitsu Limited, Kanagawa, Japan

[21] Appl. No.: 495,801

[22] Filed: Mar. 16, 1990

[30] Foreign Application Priority Data

Mar. 17, 1989 [JP] Japan ................................. 1-67281

[51] Int. Cl.$^5$ .................................................... G06F 15/00
[52] U.S. Cl. .................................. 364/413.13; 128/653.1
[58] Field of Search ...................... 364/413.43, 413.22; 324/200, 245, 248; 358/110; 361/38, 400; 250/363; 128/653, 630, 653 R, 731

[56] References Cited

U.S. PATENT DOCUMENTS

| | | | |
|---|---|---|---|
| 4,591,998 | 5/1986 | Kuperman et al. | 395/118 |
| 4,644,336 | 2/1987 | Mark | 340/701 |
| 5,072,384 | 12/1991 | Doi et al. | 364/413.13 |

FOREIGN PATENT DOCUMENTS 85304151 12/1985 European Pat. Off. .

OTHER PUBLICATIONS

"William L. Hart" Analytic Geometry and Calculus, 1957, p. 42 FIG. 27.
Samuel J. Williamson and Lloyd Kaufman; Application of SQUID Sensors to the Investigation of Neural Activity in the Human Brain, IEEE Transaction on Magnetics, vol. Mag-19, No. 3, May 1983.
Joachim Hohnsbein; Biomagnetismus Bild Der Wissenschaft Aug. 1986, pp. 76-83.

Primary Examiner—Roy N. Envall, Jr.
Assistant Examiner—Khai Tran
Attorney, Agent, or Firm—Armstrong, Westerman, Hattori, McLeland & Naughton

[57] ABSTRACT

An estimated current dipole displaying system in which a weak magnetic field generated from the heart or brain is measured to estimate the position, direction, magnitude and depth from a body surface of a current dipole which is equivalent to a heart current or a current flowing in a nerve and the estimated current dipole is displayed on a two-dimensional display. A parameter, other than that used to indicate the magnitude and those inappropriate for combined use with the magnitude indicating parameter, is used as a depth indicating parameter and the current dipole is thus displayed.

12 Claims, 15 Drawing Sheets

DIPOLE MAGNITUDE · THICKNESS
DIPOLE DEPTH · LIGHTNESS

DIPOLE MAGNITUDE · THICKNESS
DIPOLE DEPTH · HUE

DIPOLE MAGNITUDE · THICKNESS
DIPOLE DEPTH · SHAPE

DIPOLE MAGNITUDE · THICKNESS
DIPOLE DEPTH · SATURATION

DIPOLE MAGNITUDE · THICKNESS
DIPOLE DEPTH · LENGTH

DIPOLE MAGNITUDE · SHAPE
DIPOLE DEPTH · THICKNESS

DIPOLE MAGNITUDE · SHAPE
DIPOLE DEPTH · LENGTH

DIPOLE MAGNITUDE · SHAPE
DIPOLE DEPTH · REDUCED-SCALE FACTOR

DIPOLE MAGNITUDE · SHAPE
DIPOLE DEPTH · LIGHTNESS

DIPOLE MAGNITUDE · SHAPE
DIPOLE DEPTH · SATURATION

DIPOLE MAGNITUDE · SHAPE
DIPOLE DEPTH · HUE

SYSTEM FOR DISPLAYING AN ESTIMATED CURRENT SOURCE

BACKGROUND OF THE INVENTION

The present invention relates to a system for displaying on a two-dimensional display current estimated from measurement of biomagnetism.

Weak magnetic fields generated in the heart and the brain have been measured and displayed recently by a superconducting quantum interference device (SQUID). These measurements are used to estimate the currents flowing through the heart or the nerves which give rise to these magnetic fields. Such bioelectric currents are considered to be current dipoles in which a current flows through a small distance. The position, direction, magnitude and depth from a body surface of such current dipoles need to be clearly displayed on a two-dimensional display.

Heretofore, only magnetic field components perpendicular to the body surface have been measured. These measurements have been made from above the heart by a SQUID flux meter. The position, magnitude and direction of the current dipole have also been estimated. As shown in FIG. 1, these are indicated on a two-dimensional display by an arrow 1 superimposed on an image (iso map) 2. The iso map 2 also shows constant magnetic field lines.

However, the arrow 1 does not indicate the depth from the body surface at which the current dipole exists. This makes diagnosis difficult with the conventional method.

SUMMARY OF THE INVENTION

An object of the present invention is to determine not only the position, direction and magnitude of a current dipole but also its depth.

A feature of the present invention resides in a display system for displaying on a two-dimensional display an estimated current dipole estimated for the measurement of biomagnetism, characterized in that, the position and direction of the estimated current dipole are indicated by the position and direction, respectively, of an arrow, the magnitude is indicated by the length of the arrow, and the depth from the body surface is indicated by one of the display parameters thickness, shape, lightness, saturation or hue of the arrow on the two-dimensional display.

DETAILED DESCRIPTION OF THE PREFERRED EMBODIMENT OF THE PRESENT INVENTION

Figure 2:
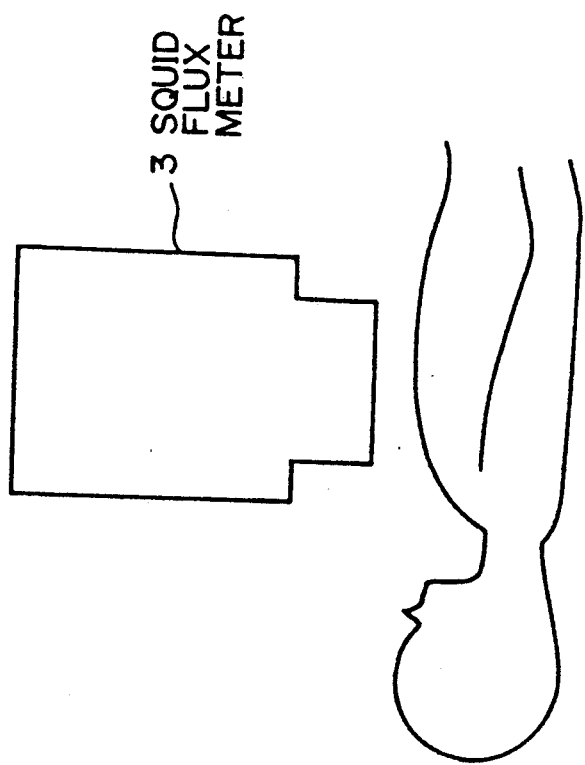
FIG. 2 is a diagram for explaining the biomagnetism measurement method.

First, the procedure of the present invention for measuring biomagnetism and displaying a magnetic field as an iso map will be described with reference to FIGS. 2 and FIGS. 3(a) to 3(b).

Magnetic field components perpendicular to the body surface are measured from above the heart by a SQUID flux meter 3. These measurements are then processed for display, resulting in an iso map, such as that shown in FIG. 3(a). The portion indicated by oblique lines in FIG. 3(b) corresponds to the iso map area of FIG. 3(a).

Figures 3A, 3B:
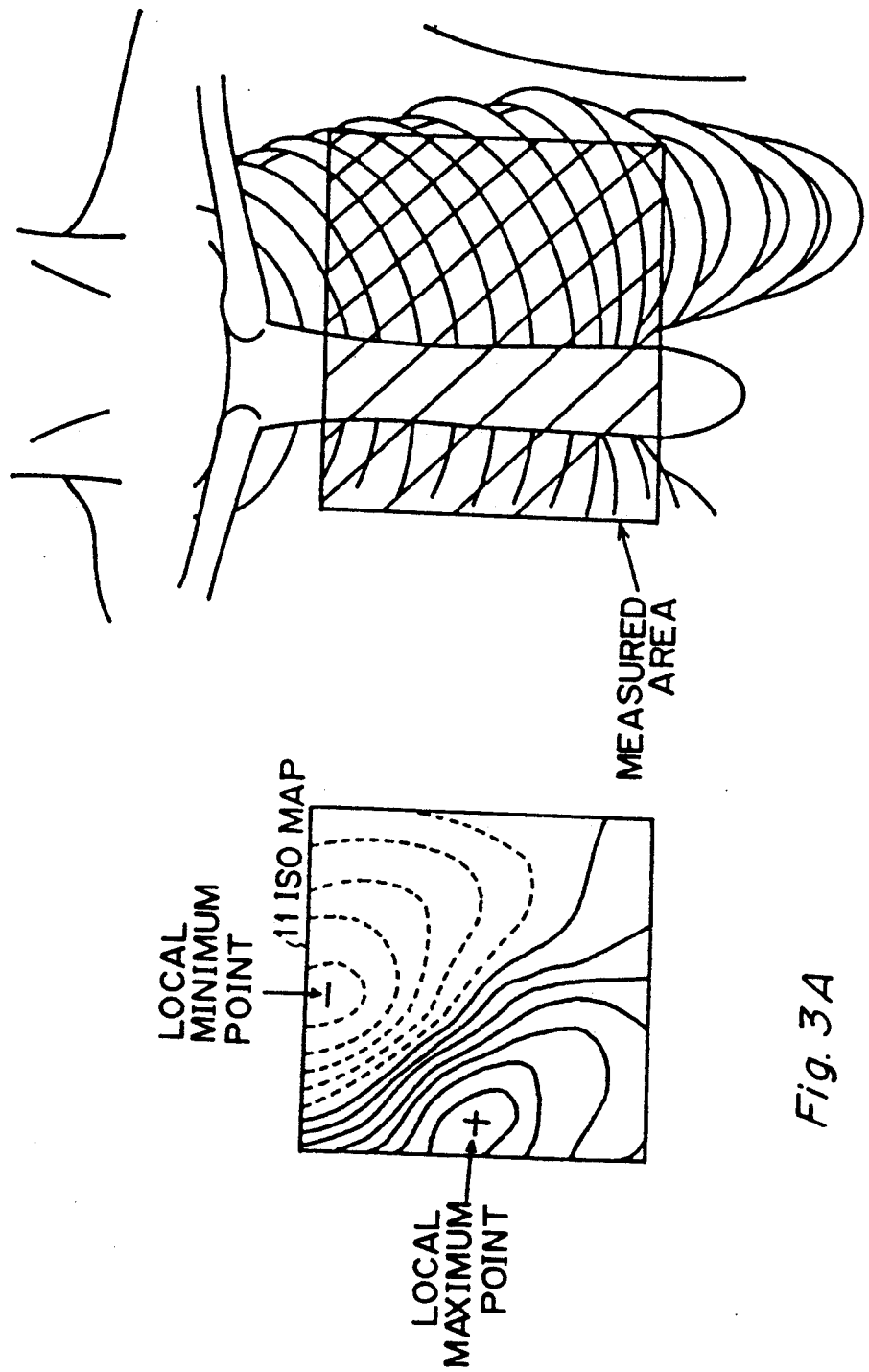
FIG. 3 illustrates an example of biomagnetism measurements.

In FIG. 3(a), the solid lines represent magnetic field components directed upward with respect to the paper and the dotted lines represent magnetic field components directed downward. The current dipole is located midway between the local maximum point of the upward magnetic field components and the local maximum point of the downward magnetic field components, i.e., the local minimum point of the upward magnetic field components, and at a depth proportional to the distance between the local maximum points. The current dipole points in the direction defined by the right-hand rule and parallel with the body surface. Thus, the position, direction, depth and magnitude of the current dipole can be found from the local maximum and minimum points of the iso map of FIG. 3(a). It should be noted that the magnitude of the current dipole can be obtained, for example, from the field strength at the local maximum point.

Figure 1:
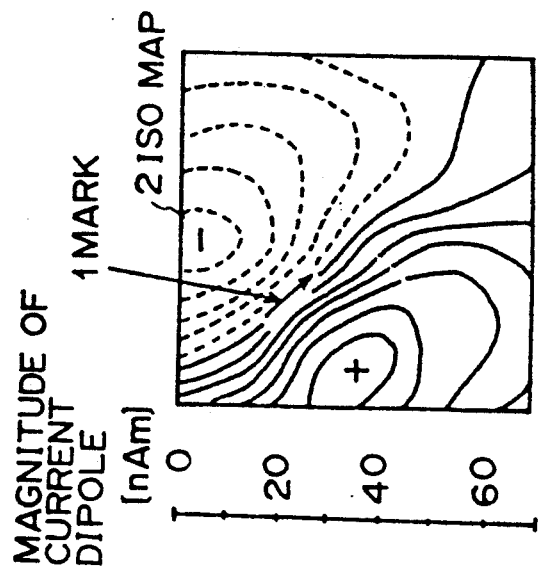
FIG. 1 illustrates an example of a conventional biomagnetism display.

The position, direction, magnitude and depth from the body surface of the current dipole are determined as described above and indicated on a screen by an arrow. The position and direction of the current dipole are indicated by the position and direction of the arrow as in FIG. 1, but its magnitude and depth are indicated by other parameters of the arrow. For example, if the magnitude of the current dipole is indicated by the length of the arrow, then other parameters, such as thickness, shape, reduced-scale factor, lightness, saturation and hue of the arrow, may be used to indicate the depth of the current dipole. Thus, if, for example, the depth is indicated by the thickness of the arrow, current dipoles of different magnitudes but the same depths will be displayed by arrows of different lengths but the same thickness.

Therefore, observation of an arrow superimposed upon an iso map on a display screen, such as those shown in FIG. 3(a), enables position, direction, magnitude and depth of a current dipole to be readily recognized.

Figure 4:
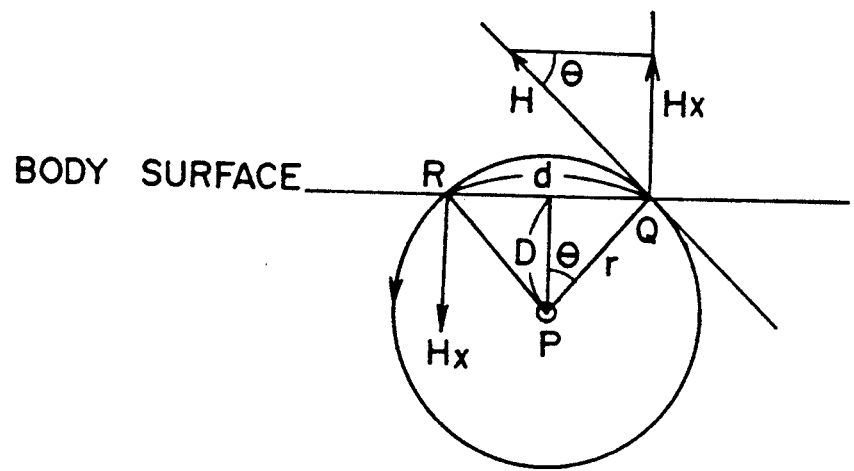
FIG. 4 illustrates the relation between a current dipole and a body surface.

FIG. 4 illustrates a model representing a relation between a current dipole and a body surface for calculating the depth and magnitude of the current dipole in the present invention. It is first assumed that the current dipole exists at a point P and a depth D from the body surface and parallel with the body surface. If the magnetic field at a point Q a distance of r from the current dipole is H and its upward component perpendicular to the body surface is Hx, the following relations hold $$H = M/r^2 \tag{1}$$

$$Hx = H \sin\theta = M \sin\theta / r^2 \tag{2}$$

where M is for the magnitude of the current dipole.

By differentiating Hx with respect to r and replacing the result of the differentiation by zero, the relation between r at which Hx assumes an extreme value and D will be given by $$r^2 = 3/2 D^2 \tag{3}$$

The relation among the point Q, the point R at which Hx is local minimum (the downward field is local maximum) and the distance d is given by $$D = d/\sqrt{2} \tag{4}$$

Also, the extreme value Hm of the magnetic field and the magnitude of the current dipole is given by $$M = \sqrt{27}/2 \, D^2 Hm \tag{5}$$

Figure 5:
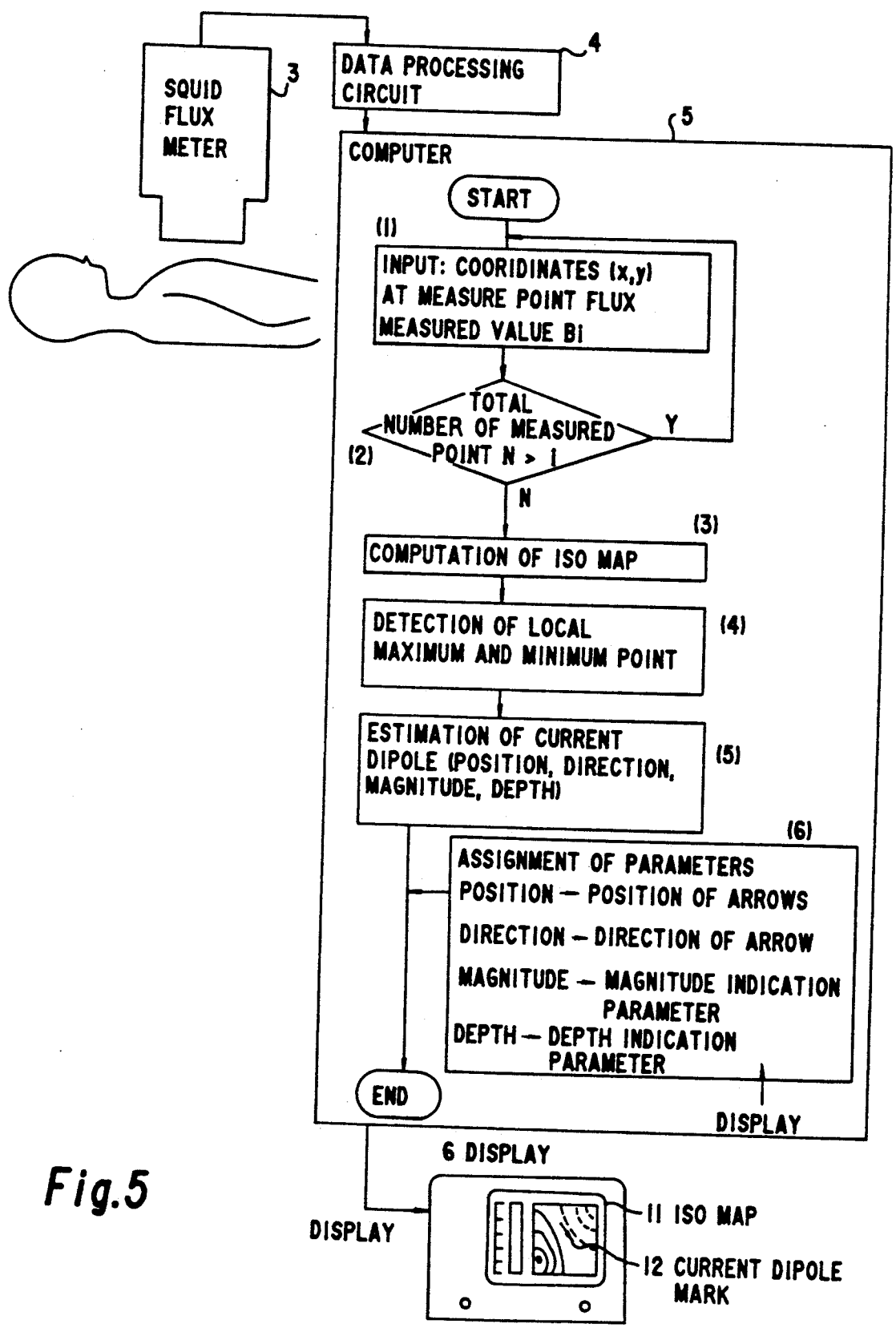
FIG. 5 is a flowchart for explaining the entire process of a display system of the present invention.

FIG. 5 is a flowchart illustrating the entire process of the current source display system of the present invention. A distribution of only magnetic field components which are perpendicular to the body surface is measured from above the heart by the use of a SQUID flux meter 3. The results of the measurement are then entered into a computer 5 via a data processing circuit 4. The data processing circuit 4 controls the SQUID flux meter 3 and acts as an interface for entering data measured by the SQUID flux meter 3 into the computer 5. The computer 5 performs steps ① to ⑤ to display a current dipole mark 12 superimposed on such an iso map 11 indicating iso maps, such as that shown in FIG. 3. Steps ① to ⑤ are described below.

In ①, the co-ordinates (x, y) of a measured point i and a magnetic field component Bi perpendicular to the body surface measured by the SQUID flux meter 3 are received as input signals.

In step ②, a test is made to determine whether or not the total number of measured points N exceeds i. If it does, step ① is repeated. If not, the steps following step ② are carried out.

In the above process, the co-ordinates (x, y) of, for example, 6×6 (=36) measured points on the body surface and the magnetic field components Bi, are entered into the computer 5.

In step ③, an iso map is computed. This means that an iso map formed of solid and dotted iso maps, as shown in FIG. 3, is computed on the basis of the co-ordinates (x, y) of the measured points and the magnetic field components Bi entered in steps ① and ②.

In step ④, the local maximum and minimum points, i.e., the local maximum and minimum points indicated by "+" and "−" in FIG. 3, are detected.

In step ⑤, the position, direction, magnitude and depth of the current dipole are estimated. More specifically, as described above, the point midway between the local maximum and minimum points detected in step ④ is estimated to be the position of the current dipole, the value $1/\sqrt{2}$ times the distance between the local maximum and minimum points is estimated to be the depth at which the current dipole exists, the direction determined by the right-hand rule is estimated to be the direction of the current dipole and the magnitude of the current dipole is estimated on the basis of the measured magnetic field component Bi.

As shown, in step ⑥, the position, direction, magnitude and depth of the current dipole estimated in step ⑤ are assigned to the position, direction, magnitude and depth indicating parameters of the current dipole arrow mark 12. The current dipole mark 12 is superimposed upon the iso map 11 on the display 6 in step ⑤.

Figure 6B:
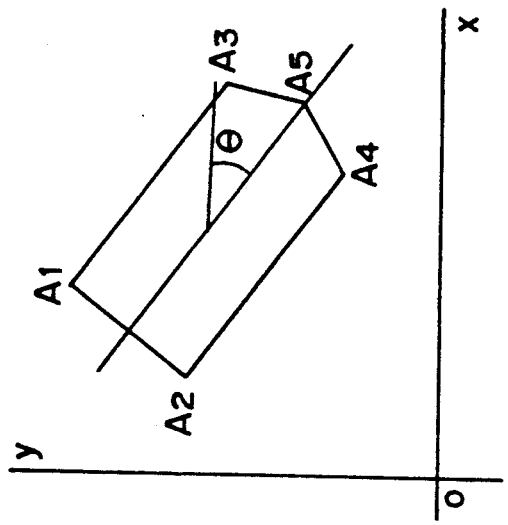
FIGS. 6(a) and 6(b) are a diagram for explaining a method of calculating the position of a current-dipole displaying arrow.
Figure 6A:
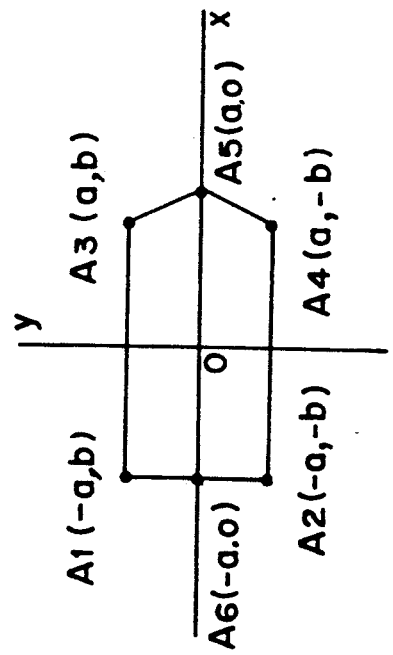

FIGS. 6(a) and 6(b) are diagram illustrating a method of computing the position of the arrow indicating the current dipole. FIG. 6(a) illustrates an original figure of the display arrow. The original figure represents an arrow having corners A1 to A4 of a rectangle with sides 2a and 2b centered at the origin of an x-y plane, and another corner at a point A5 on the X axis outside the rectangle. When it has no thickness, the arrow is represented by points A3, A4, A5 and the point A6 at which the line connecting A1 and A2 intersect the X axis.

FIG. 6(b) illustrates a display example of the original figure, enlarged, shifted and rotated according to values of the indicating parameters. In general, when a point (Aix, Aiy) is rotated through an angle $\theta$ and shifted by X in the direction of the x axis and by Y in the direction of the y axis, the co-ordinates of the points will be given by $$Xi = Aix \cos\theta - Aiy \sin\theta + X$$

$$Yi = Aix \sin\theta + Aiy \cos\theta + Y \tag{6}$$

Figure 7:
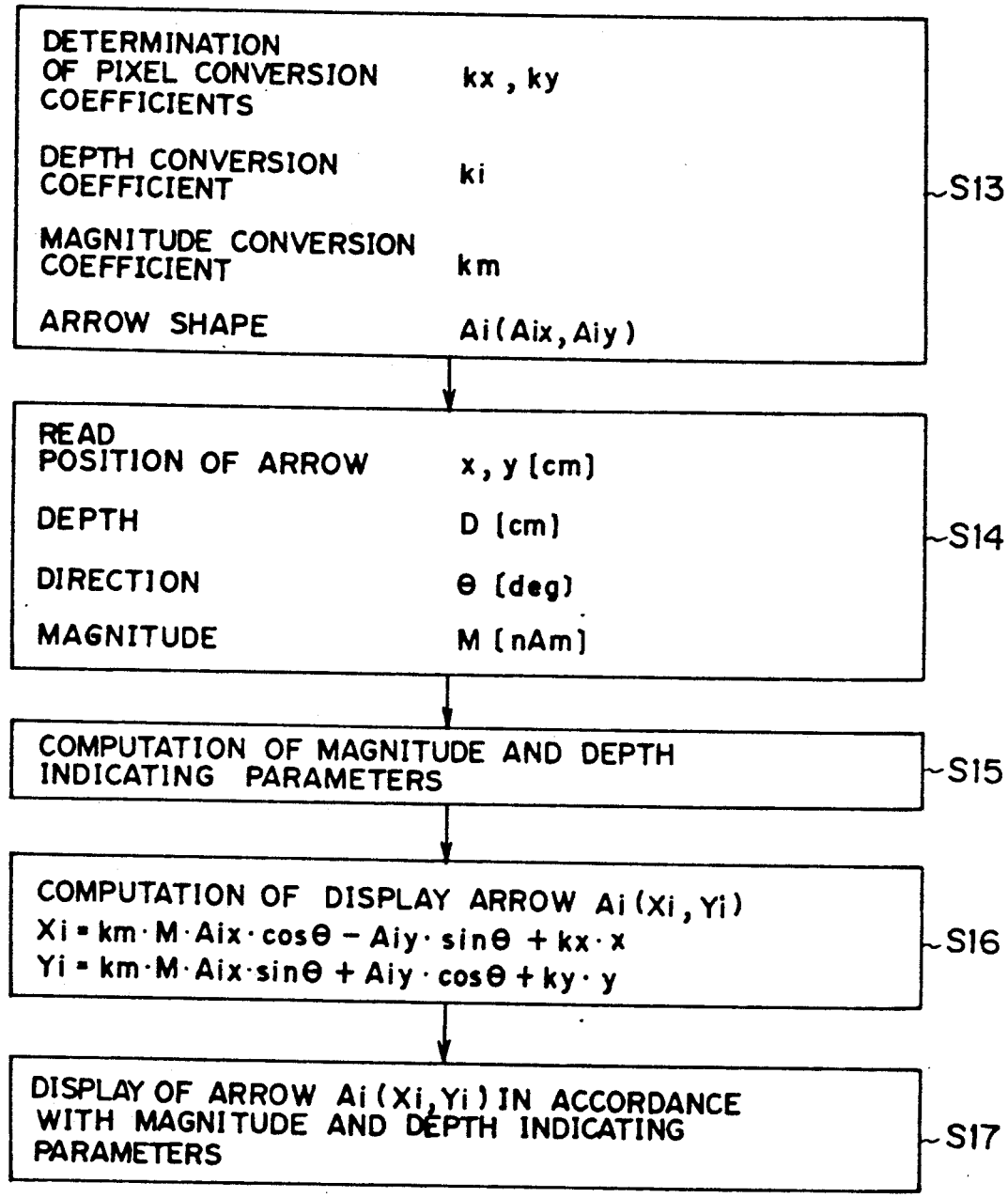
FIG. 7 is a flowchart for explaining the process of displaying the current dipole.

For example, when the arrow of FIG. 6(a) is lengthened by a factor of $k_m \times m$, rotated through an angle $\theta$, and shifted by $K_y \times y$ toward the y axis and the $k_x \times x$ toward the x axis, the co-ordinates of the apexes will be given by $A_1(-k_m ma \cos\theta - b \sin\theta + k_x X, \; -k_m ma \sin\theta + b \cos\theta + k_y y)$ $A_2(k_m ma \cos\theta - b \sin\theta + k_x X, \; k_m ma \sin\theta + b \sin\theta + k_y y)$ $A_3(k_m mc \cos\theta + k_x X, \; k_m mc \sin\theta + k_y y)$ $A_4(k_m ma \cos\theta + b \sin\theta + k_x X, \; k_m ma \sin\theta - b \sin\theta + k_y y)$ $A_5(-k_m ma \cos\theta + b \sin\theta + k_x X, \; -k_m ma \sin\theta - b \sin\theta + k_y y)$ FIG. 7 is a flowchart illustrating the process of displaying the current dipole. Determined in step (S)13 are pixel conversion coefficients kx and ky (K = kx×x, Y=ky×y) for converting an actual position of the dipole to positions X and Y of a pixel on the display screen; a magnitude conversion coefficient km for converting the magnitude M (nA×m) of the dipole to a magnitude indicating parameter of the display arrow, for example, the length of the arrow; a depth conversion coefficient Ke for converting the depth D of the dipole to a depth indicating parameter of the display arrow, for example, the lightness of the display arrow; and the shape of the arrow, that is, each corner of the original figure of the display arrow of FIG. 6(a). Next, in step S14, the position x, y, the direction θ, the magnitude M and the depth D of the current dipole are read.

In step S15, the magnitude indicating parameter of the display arrow, e.g., the lengthening of the display arrow, and the depth indicating parameter, e.g., the lightness of the arrow, are calculated. In step S16, the position of each corner of the display arrow on the display screen is calculated. The formulas for calculating the x and y co-ordinates of corners A1 to A4 explained with reference to FIG. 6(b) are indicated. In step S17, the arrow is displayed in accordance with the previously set depth indicating parameter and magnitude indicating parameter. For example, the inside of the arrow will be displayed by the lightness of the depth indicating parameter.

Figure 8A:
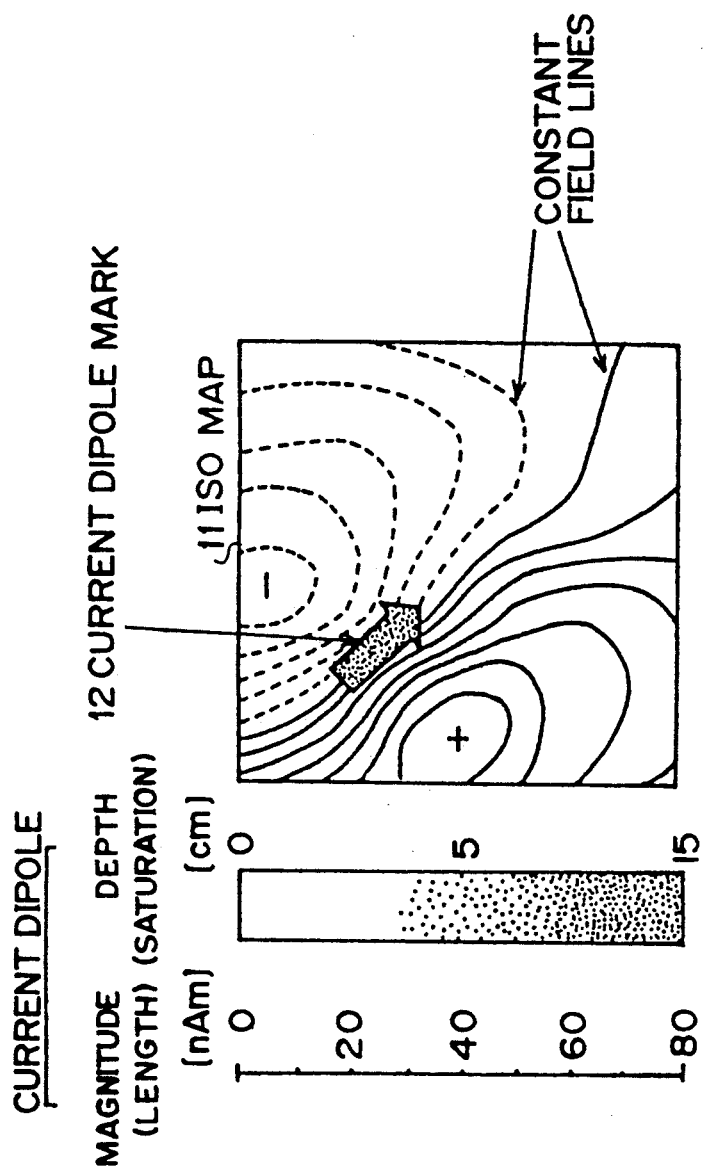
FIGS. 8(a) and 8(b) illustrate a display example of an iso map and a current dipole.
Figure 8B:
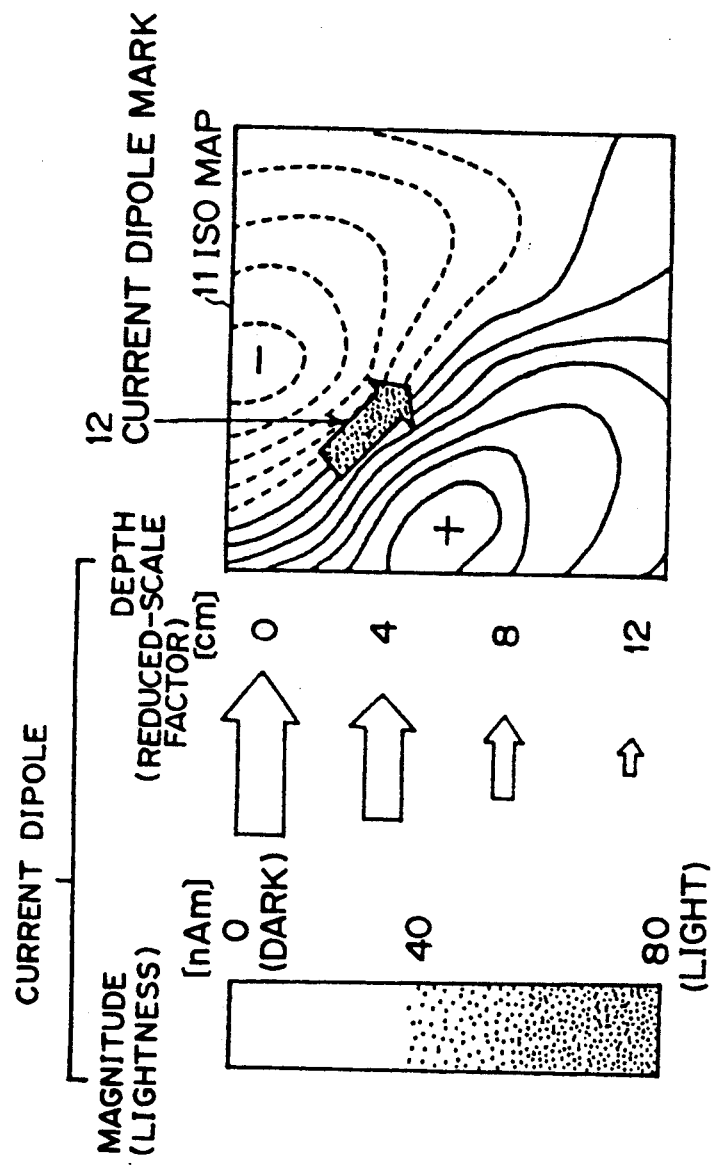
Figure 9C:
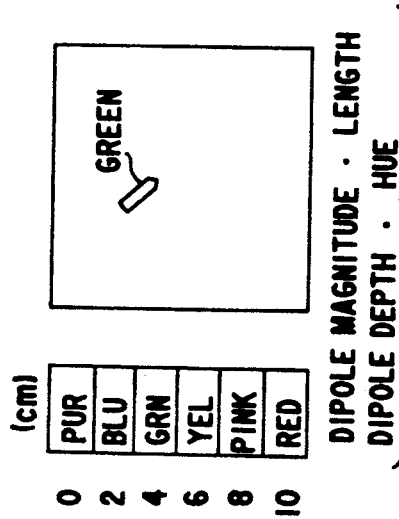
FIGS. 9(a) to 9(e) illustrate examples of a dipole display when the magnitude of a current dipole is indicated by the length of an arrow.
Figure 9E:
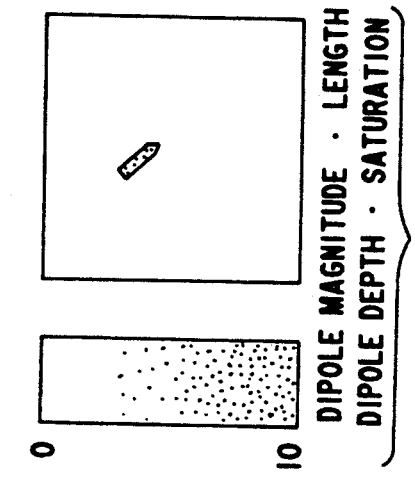
Figure 9B:
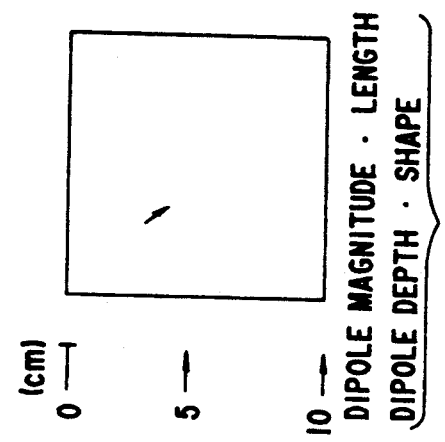
Figure 9D:
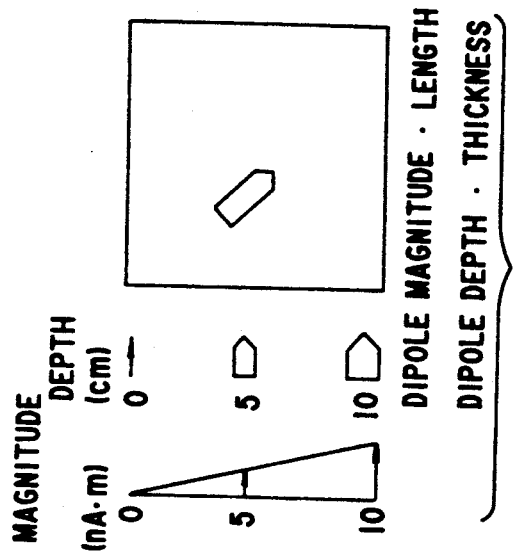
Figure 9A:
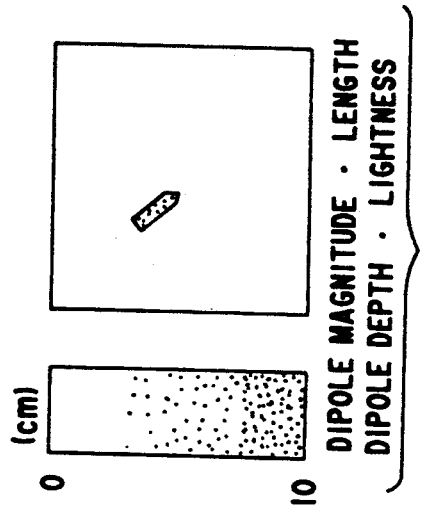
Figure 10C:
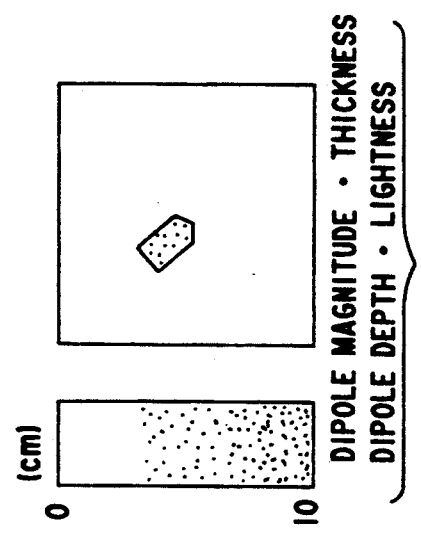
FIGS. 10(a) to 10(e) illustrate examples of a dipole display when the magnitude of a current dipole is indicated by the thickness of an arrow.
Figure 10E:
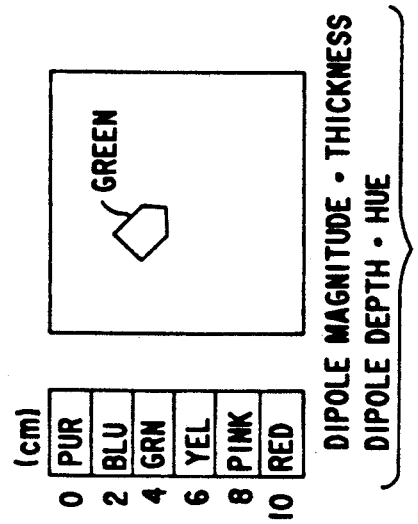
Figure 10B:
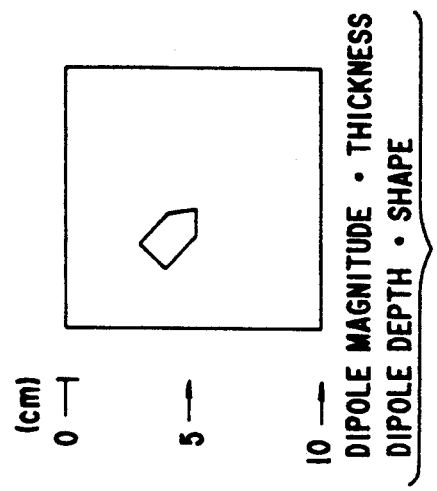
Figure 10D:
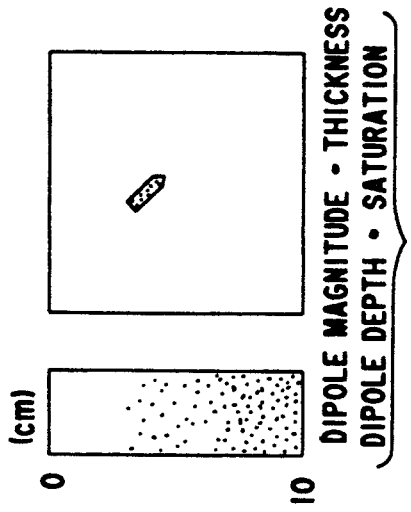
Figure 10A:
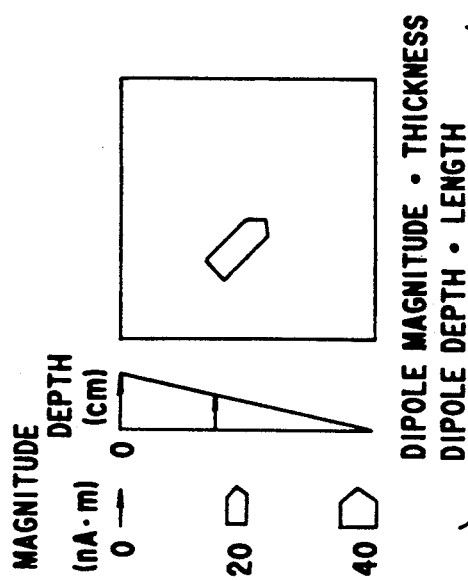

FIGS. 8(a) and 8(b) illustrate display examples of the iso map and the current dipole. In FIG. 8(a), the magnitude and depth of the current dipole are illustrated by length and saturation, respectively, of the arrow, while in FIG. 8(b), the magnitude and depth of the current dipole are indicated by the lightness and the reduced-scale factor of the arrow, respectively. The magnitude of the current dipole shown on the left-hand side of FIG. 8(a) indicates the magnitude (current dipole magnitude, for example, 20 nAm (nano ampere meter)) to which the length of the current dipole mark 12 corresponds. [nAm] is a unit of magnitude of the current dipole and a product of current [A] and length [m].

Also, the scale of depth (saturation) of the current dipole of FIG. 8(a) indicates the depth (for example, 5 cm) of the current dipole from the body surface, based on the saturation of the current dipole mark 12 displayed on the iso map 11.

The scale of magnitude (lightness) of the current dipole of FIG. 8(b) indicates the magnitude of the current dipole, based on the lightness of the current dipole mark 12 displayed on the iso map 11. The scale of depth (reduced-scale factor) indicates the depth (for example, 4 cm) based on the current dipole 12 displayed on the iso map 11.

FIG. 9(a) to 9(e) illustrate display examples of the current dipole in which its magnitude is indicated by the length of the arrow. The depth of the dipole is indicated by the thickness of the arrow in (a); by the shape of the arrow, i.e., the opening angle of the arrow head in (b); by the lightness of the arrow in (c); and by the saturation of the arrow in (d); and hue of the arrow in (e).

FIGS. 10(a) to 10(e) illustrate display examples of the current dipole in which the magnitude of the current dipole is indicated by the thickness of the arrow. The depth of the dipole is indicated by the length of the arrow in (a), by the shape of the arrow in (b), by the lightness of the arrow in (c), by the saturation of the arrow in (d) and by the hue of the arrow in (e).

Figure 11A:
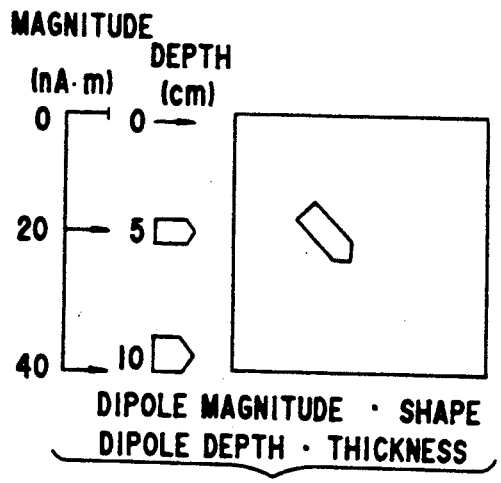
FIGS. 11(a) to 11(f) illustrate examples of a dipole display when the magnitude of a current dipole is indicated by the shape of an arrow.
Figure 11B:
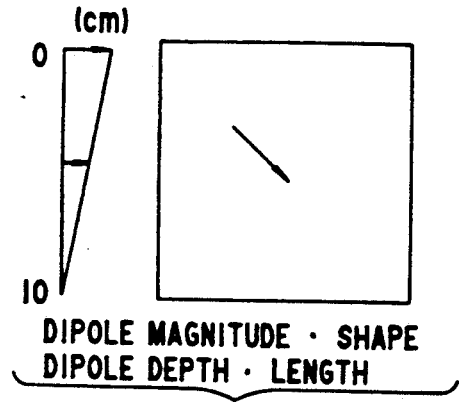
Figure 11C:
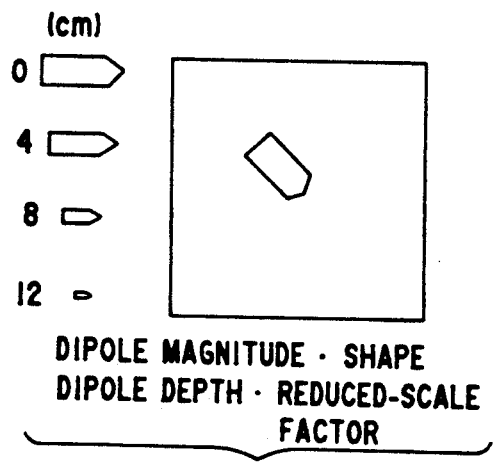
Figure 11D:
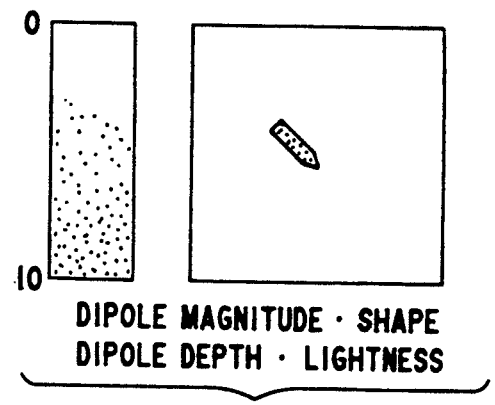
Figure 11E:
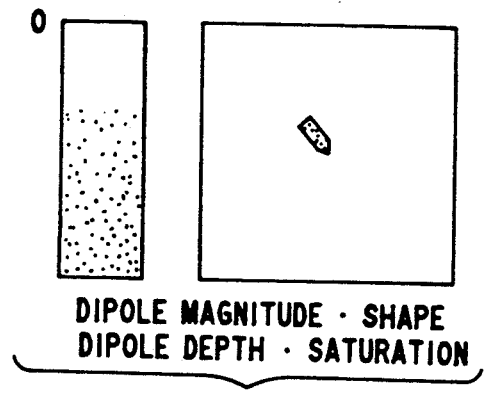
Figure 11F:
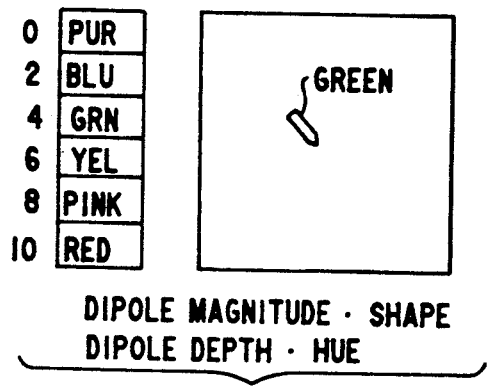

FIGS. 11(a) tio 11(f) illustrate display examples of the current dipole in which the magnitude of the current dipole is indicated by the shape of the arrow, that is, the angle between the arrowhead and the arrow axis. The depth of the dipole is indicated by the thickness of the arrow in (a), by the length of the arrow in (b), by the reduced-scale factor of the arrow in (c), by the lightness of the arrow in (d), by the saturation of the arrow in (e) and by the hue of the arrow, in (f).

Figure 12A:
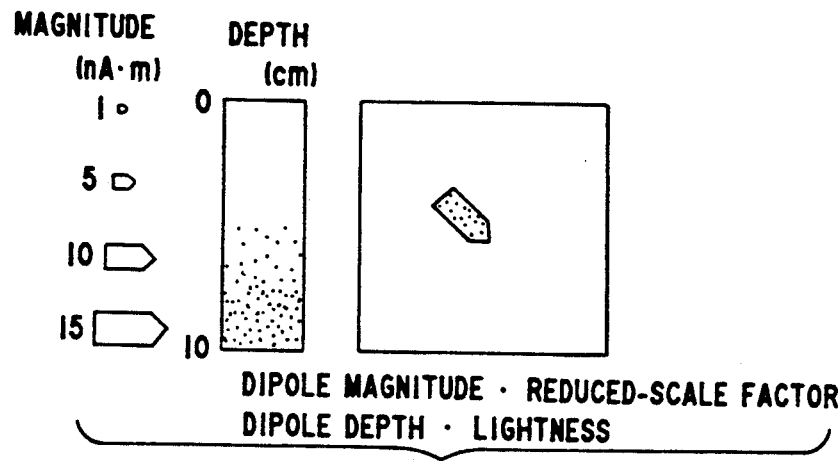
FIGS. 12(a) to 12(c) illustrate examples of a dipole display when the magnitude of a current dipole is represented by the reduced-scale factor of an arrow.
Figures 12B, 12C:
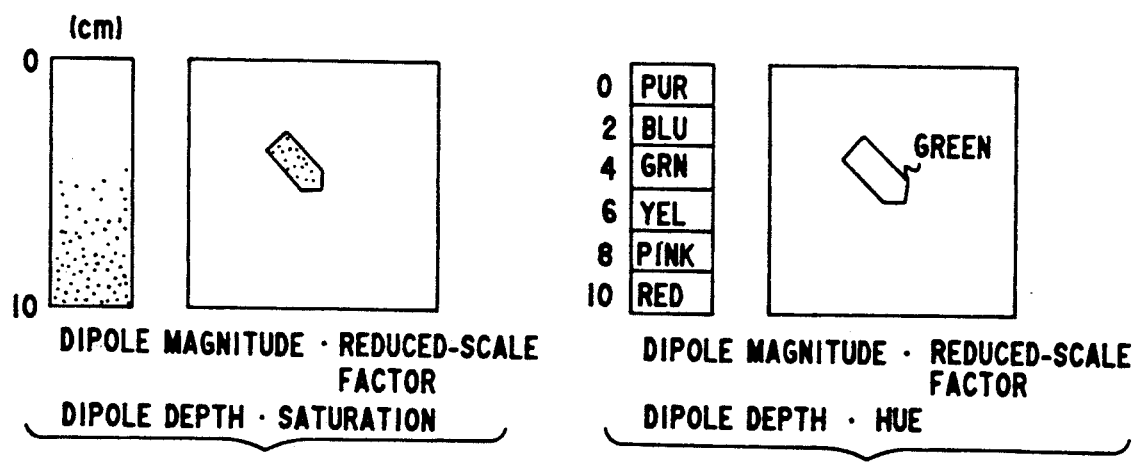
Figure 13A:
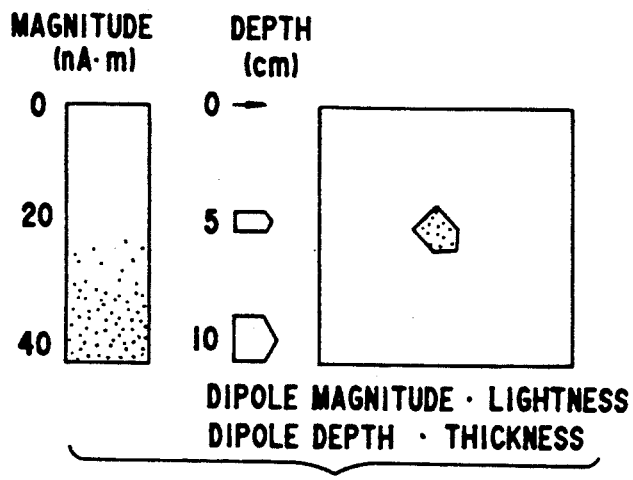
FIGS. 13(a) to 13(f) illustrate examples of a dipole display when the magnitude of a current dipole is represented by the lightness of an arrow.
Figure 13B:
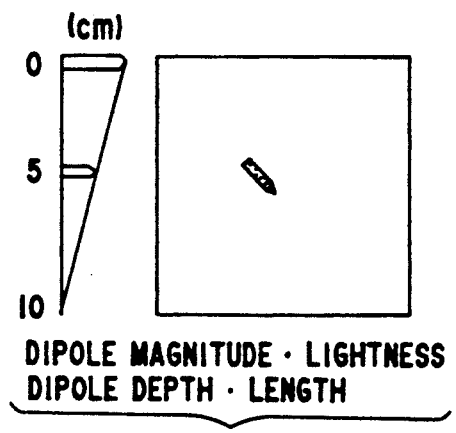
Figure 13C:
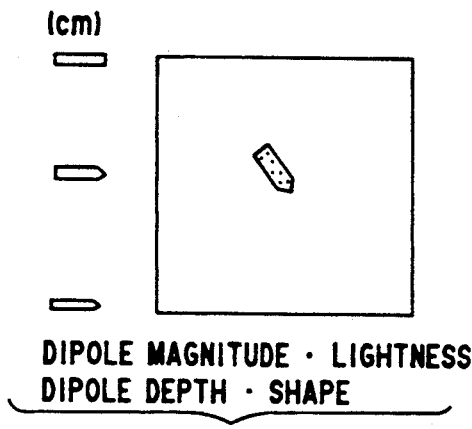
Figure 13D:
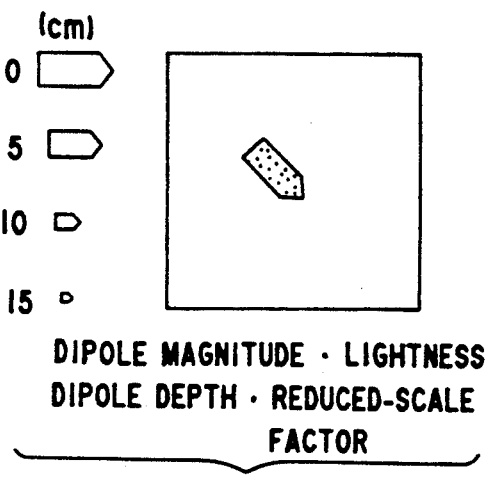
Figure 13E:
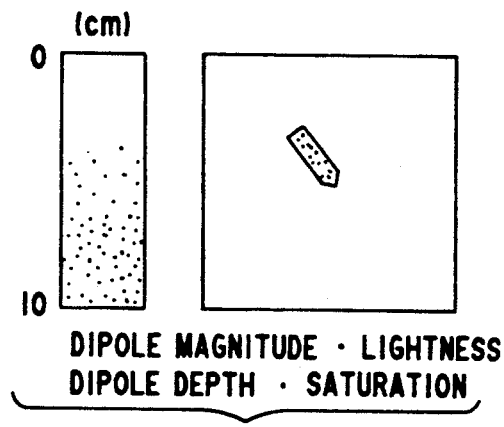
Figure 13F:
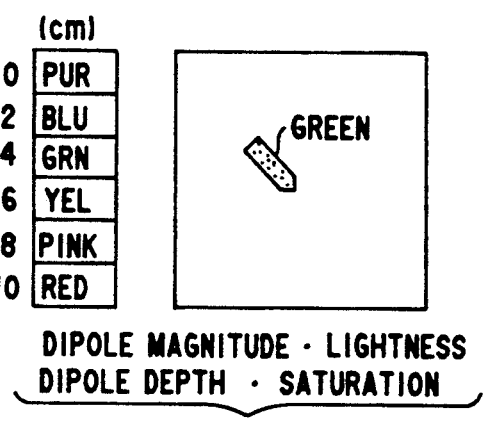
Figure 14A:
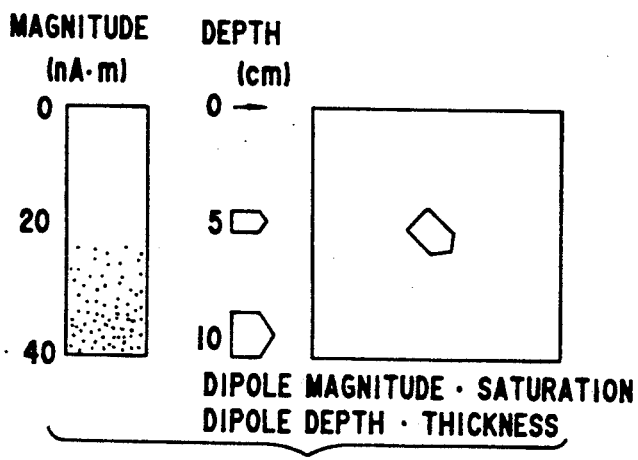
FIGS. 14(a) to 14(f) illustrate examples of a dipole display when the magnitude of a current dipole is represented by the saturation of an arrow.
Figure 14B:
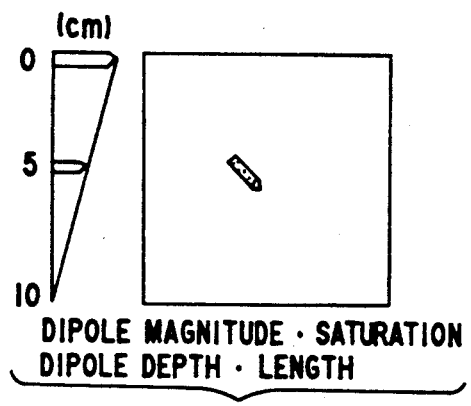
Figure 14C:
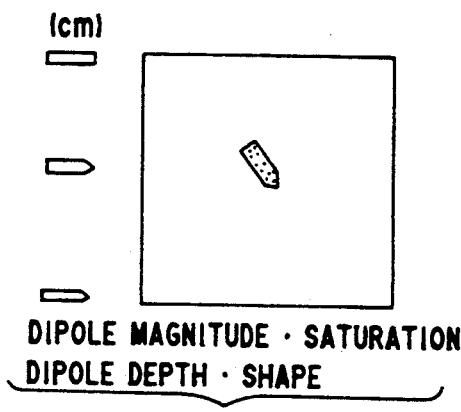
Figure 14D:
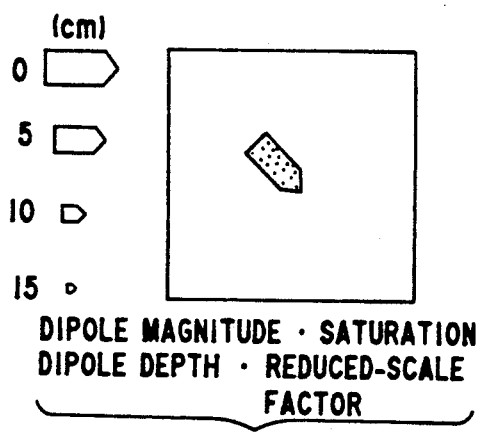
Figure 14E:
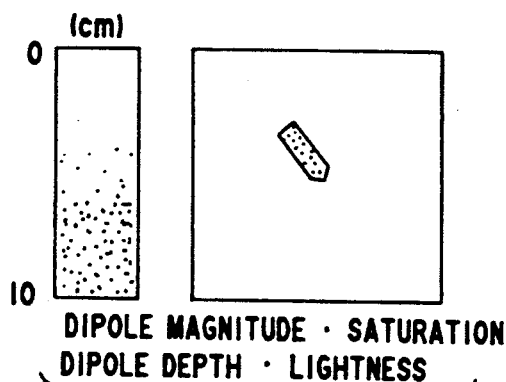
Figure 14F:
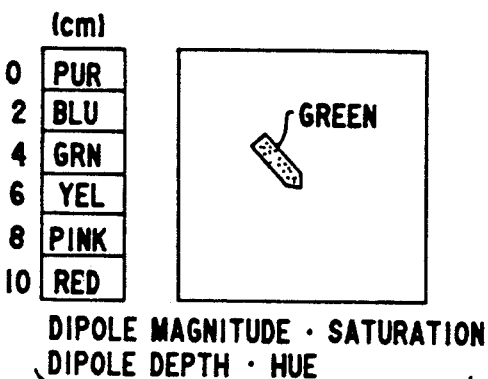
Figure 15A:
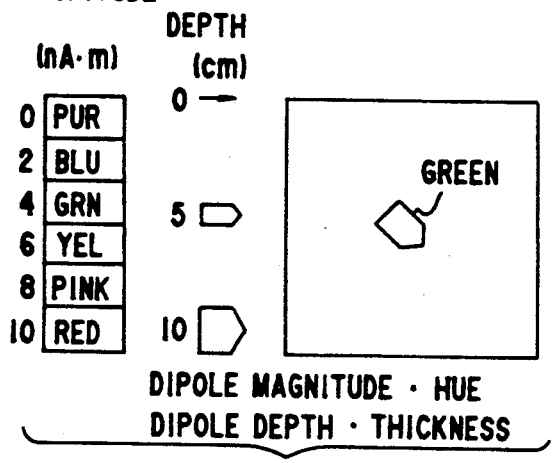
FIGS. 15(a) to 15(f) illustrate examples of a dipole display when the magnitude of a current dipole is represented by the hue of an arrow.
Figure 15B:
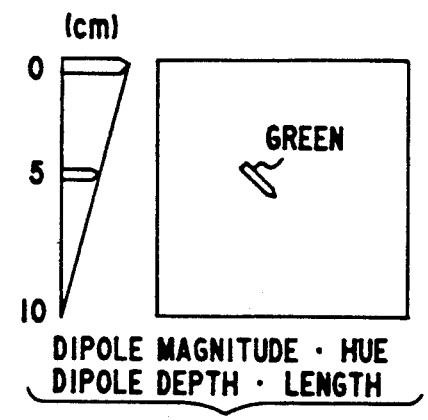
Figure 15C:
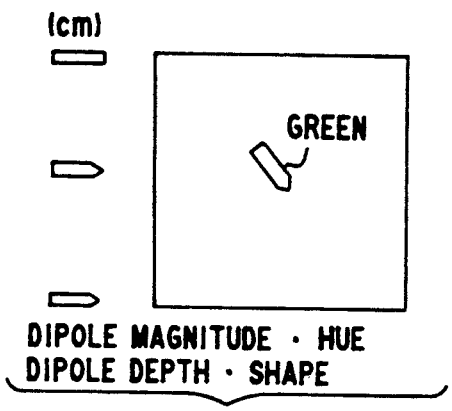
Figure 15D:
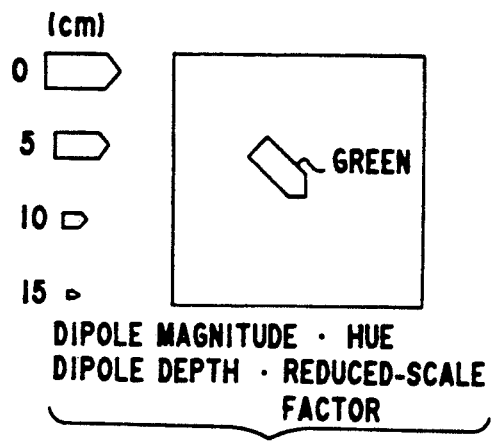
Figure 15E:
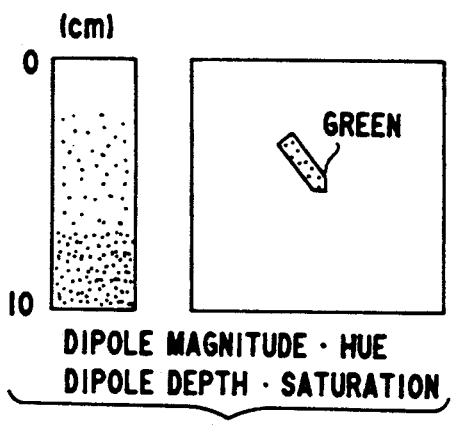
Figure 15F:
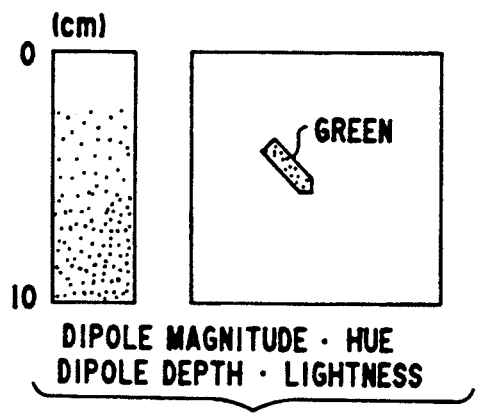

FIGS. 12(a) to 12(c) illustrate display examples of the current dipole in which the magnitude of the current dipole is indicated by the reduced-scale factor of the arrow. The depth of the dipole is indicated by the lightness of the arrow in (a), by the saturation of the arrow in (b) and by the hue of the arrow in (c).

FIGS. 13(a) to 13(f) illustrate display examples of the current dipole in which the magnitude of the current dipole is indicated by the lightness of the arrow. The depth of the dipole is indicated by the thickness of the arrow in (a), by the length of the arrow in (b), by the shape of the arrow in (c), by the reduced-scale factor of the arrow in (d), by the saturation of the arrow in (e) and by the hue of the arrow in (f).

FIGS. 14(a) to 14(f) illustrate display examples of the current dipole in which the magnitude of the current dipole is indicated by the saturation of the arrow. The depth of the dipole is indicated by the thickness of the arrow in (a), by the length of the arrow in (b), by the shape of the arrow in (c), by the reduced-scale factor of the arrow in (d), by the lightness of the arrow in (e) and by the hue of the arrow in (f).

FIGS. 15(a) to 15(f) illustrate display examples of the current dipole in which the magnitude of the current dipole is indicated by the hue of the arrow. The depth of the dipole is indicated by the thickness of the arrow in (a), by the length of the arrow in (b), by the shape of the arrow in (c), by the reduced-scale factor of the arrow in (d), by the saturation of the arrow in (e) and by the lightness of the arrow in (f).

As described above, an estimated current dipole displaying system in which a weak magnetic field generated from the heart or brain is measured to estimate the position, direction, magnitude and depth from a body surface of a current dipole which is equivalent to a heart current or a current flowing in a nerve and the estimated current dipole is displayed on a two-dimensional display. The positions of local maximum and minimum points of the magnetic field perpendicular to the body surface and extreme values of the magnetic field are measured from above the body surface to estimate the position of the current dipole. The position and direction of the current dipole are indicated by the position and direction of an arrow on a two-dimensional display. Its magnitude is indicated by one of the indicating parameters length, thickness, shape, reduced-scale factor, saturation or lightness of the arrow. A parameter, other than that used to indicate the magnitude and those inappropriate for combined use with the magnitude indicating parameter, is used as a depth indicating parameter and the current dipole is thus displayed.

The display system of the present invention is useful in displaying a current dipole acting as a source of a weak magnetic field generated from the heart and brain.

What is claimed is:

1. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the magnitude of the estimated current dipole by controlling a length of the arrow on the two-dimensional display; and said display control means indicating a depth from the body surface by controlling one of a group of display parameters thickness, shape, lightness, saturation or hue of the arrow on the two-dimensional display.

2. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the magnitude of the estimated current dipole by controlling a thickness of the arrow on the two-dimensional display; and said display control means indicating a depth from the body surface by controlling one of a group of display parameters length, shape, lightness, saturation or hue of said arrow on said two-dimensional display.

3. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the magnitude of the estimated current dipole by controlling a shape of said arrow on the two-dimensional display; and said display control means indicating a depth from the body surface by controlling one of a group of display parameters lightness, saturation or hue of the arrow on said two-dimensional display.

4. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the magnitude of the estimated current dipole by controlling a scale of the arrow on the two-dimensional display; and said display control means indicating a depth from the body surface by controlling one of a group of display parameters lightness, saturation or hue of said arrow on said two-dimensional display.

5. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the magnitude of the estimated current dipole by controlling a lightness of said arrow on the two-dimensional display; and said display control means indicating a depth from the body surface by controlling one of a group of display parameters thickness, lightness, shape, saturation or hue of the arrow on said two-dimensional display.

6. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display control means indicating the display of the magnitude of the estimated current dipole by controlling a saturation of said arrow on the two-dimensional display; and said display control means indicating a depth from a body surface by controlling one of a display parameters thickness, length, shape, scale, lightness, or hue of said arrow on said two-dimensional display.

7. A display system for displaying on a two-dimensional display an estimated current dipole for a measurement of biomagnetism, comprising:

display control means receiving information relating to a position, a direction, and a magnitude of the estimated current dipole below a surface of a body, for controlling the appearance of an image on the two-dimensional display; said display control means causing the two-dimensional display to indicate a position and direction of the estimated current dipole by controlling the position and the direction, respectively, of an arrow on the two-dimensional display;

said display means indicating the display of the magnitude of the estimated current dipole by controlling a hue of said arrow on the two-dimensional display; and said display control means indicating a depth from the body surface by controlling one of a group of display parameters thickness, length, shape, scale, saturation or lightness of said arrow on said two-dimensional display.

8. A display method for displaying on a two-dimensional display an estimated current dipole by a measurement of biomagnetism comprising the steps of:
   providing a two-dimensional display means for displaying indicia representing the measurement of biomagnetism;
   providing sensing means for detecting a component of a magnetic field at a surface of a body;
   providing an interface means for controlling said sensing means and for supplying an output representing the detected component of said magnetic field;
   providing computing means receiving the output of said interface means, for computing an estimate of a location, direction, and depth of the current dipole, and for controlling the appearance of an image on said two-dimensional display means; said computing means having a display control means which controls the appearance of the image on the two-dimensional display, and wherein said display control means causes the two-dimension display to indicate a position and direction of the estimated current dipole by controlling the position and the direction, respectively, of an arrow on the two-dimensional display;
   using said sensing means to detect the component of said magnetic field at the surface of the body at a plurality of locations;
   using said interface means to produce an output representing the detected component of said magnetic field at said plurality of locations, to said computing means;
   using said computing means for differentiating the detected components of the magnetic field with respect to a distance r, said detected components of the magnetic field being perpendicular to the surface of the body;
   using said computing means for determining a local minimum of the magnetic field at the surface of the body and a local maximum of the magnetic field at the surface of the body, and replacing a result of the differentiation with O to find a relation between a depth D from the surface of the body at which said current dipole exists and a value of r at which said detected component of the magnetic field assumes an extreme value;
   finding a relation between local maximum and minimum points of a magnitude of the magnetic field on the surface of the body using a predetermined formula relating the values of D and r; and
   using said computing means for finding the magnitude of said current dipole from said relation between D and r and from said relation between said local maximum and minimum points of the magnitudes of the detected components of the magnetic field.

9. A display method for displaying on a two-dimensional display an estimated current dipole from a measurement of biomagnetism comprising the steps of:
   providing a two-dimensional display means for displaying indicia representing the measurement of biomagnetism;
   providing computing means receiving measured output values representing detected values of a detected component of a magnetic field of the current dipole and for controlling the appearance of an image on said two-dimensional display means; said computing means having a display control means which controls the appearance of the image on the two-dimensional display, and wherein said display control means causes the two-dimensional display to indicate a position and direction of the estimated current dipole by controlling the position and the direction, respectively, of an arrow on the two-dimensional display;
   repeatedly entering said measured output values representing the detected components of the magnetic field of the current dipole perpendicular to a surface of a body at a plurality of points using coordinates to indicate position of each point measured on the surface of the body until a number of measured points reaches a predetermined number;
   using said computing means for deriving an iso map consisting of lines connecting points of equal magnetic field intensity from magnetic flux values at said measured points;
   using said computing means for determining local maximum and minimum points of the detected magnetic field components from said iso map;
   using said computing means for estimating the position, direction, magnitude and depth of said current dipole from aid positions of said local maximum and minimum points and from extreme values of the detected magnetic field components; and
   using said computing means for assigning the estimated position, direction, magnitude and depth of said current dipole to display parameters of the arrow on said two-dimensional display means.

10. A display system for displaying on a two-dimensional display an estimated current dipole from a measurement of biomagnetism, comprising:
    computing means receiving measured output values representing detected values of a detected component of a magnetic field of the current dipole and for controlling the appearance of an image on said two-dimensional display means; said computing means having a display control means which controls the appearance of the image on the two-dimensional display, and wherein said display control means causes the two-dimensional display to indicate a position and direction of the estimated current dipole by controlling a position and a direction, respectively, of an arrow on the two-dimensional display;
    wherein an original figure of an arrow for displaying said estimated current dipole is displayed using four corners of a rectangle centered at an origin of an x-y coordinate plane and a point of an x axis outside the rectangle, and wherein said original figure of said arrow is displayed in enlarged or reduced form, displaced parallel to the x-y coordinates according to a determined position of said current dipole and rotated according to a determined direction of said current dipole.

11. A display system for displaying on a two-dimensional display an estimated current dipole from a measurement of biomagnetism, comprising:
    computing means receiving measured output values representing detected values of a detected component of a magnetic field of the current dipole and for controlling the appearance of an image on said two-dimensional display means; said computing means having a display control means which controls the appearance of the image on the two-dimensional display, and wherein said display control means causes the two-dimensional display to indicate a position and direction of the estimated current dipole by controlling a position and a direction, respectively, of an arrow on the two-dimensional display;

wherein an original figure of an arrow is displayed for using four points, two of which are two corners of a rectangle centered at an origin of an x-y coordinate plane in a positive x direction; one of which is an intersection of a point of a line connecting the other two corners of said rectangle in a negative x direction, and an x axis; and the other of which is on the x axis in a positive x direction, outside said rectangle;

wherein said original figure of said arrow is displayed in enlarged or reduced form, displaced parallel to the x-y coordinates according to a determined position of said current dipole and rotated according to a determined direction of said current dipole.

12. A display method for displaying on a two-dimensional display an estimated current dipole by a measurement of biomagnetism, comprising the steps of:

providing a two-dimensional display means for displaying indicia representing the measurement of biomagnetism;

providing computing means receiving measured output values representing detected values of a detected component of a magnetic field of the current dipole and for controlling the appearance of an image on said two-dimensional display means; said computing means having a display control means which controls the appearance of the image on the two-dimensional display, and wherein said display control means causes the two-dimensional display to indicate a position a nd direction of the estimated current dipole by controlling the position and the direction, respectively, of an arrow on the two-dimensional display;

determing a pixel conversion coefficient for converting the position of said estimated current dipole to a position of a pixel on the display screen, determining a magnitude conversion coefficient for converting a magnitude of said current dipole to a magnitude indicating parameter of the arrow on the display screen, determining a depth conversion coefficient for converting a depth from a surface of a body at which said current dipole exists to a depth indicating parameter of said arrow, and an original figure of said arrow;

using said computing means for determining the position, direction, magnitude and depth from a body surface of said current dipole;

deriving said magnitude indicating parameter and said depth indicating parameter of said arrow for displaying said current dipole; and displaying said arrow in accordance with said magnitude indicating parameter and said depth indicating parameter.

* * * * *